United States Patent [19]

Freitas

[11] Patent Number: 5,137,509
[45] Date of Patent: Aug. 11, 1992

[54] SURGICAL INSUFFLATION INSTRUMENT

[75] Inventor: Michael W. Freitas, Irving, Tex.

[73] Assignee: Dexide, Inc., Fort Worth, Tex.

[21] Appl. No.: 687,484

[22] Filed: Apr. 17, 1991

[51] Int. Cl.$^5$ ............................................. A61M 37/00
[52] U.S. Cl. ....................................... 604/26; 604/51; 604/158
[58] Field of Search ............... 604/158, 159, 162, 264, 604/268, 51, 117, 157, 26, 168, 170, 164, 274

[56] References Cited

U.S. PATENT DOCUMENTS

| | | | |
|---|---|---|---|
| 1,527,291 | 2/1925 | Zarraquin | 604/158 |
| 3,530,492 | 9/1970 | Ferber | 604/117 |
| 3,840,008 | 10/1974 | Noiles | 604/158 |
| 4,869,717 | 9/1989 | Adair | 604/51 |

*Primary Examiner*—Cary E. O'Connor
*Attorney, Agent, or Firm*—Jackson & Walker

[57] ABSTRACT

A surgical insufflation instrument is disclosed. In one embodiment, the instrument has concentrically disposed cylindrical members with the distal end of one of the members having its outer surface contourly sloped to a closing end and having a fluid transmission passageway therethrough. In another embodiment, the insufflation instrument provides an enhanced visual indicator for determining relative telescopic expansion and contraction positions of the cylindrical members. In another embodiment, a snap and groove configuration are provided for insertion of a cap member onto the proximal end of a housing securing the concentric members.

17 Claims, 3 Drawing Sheets

SURGICAL INSUFFLATION INSTRUMENT

BACKGROUND OF THE INVENTION

(1) Field of the Invention

The invention relates to a surgical insufflation instrument and, more particularly, to a device in which a sharp implement pierces or punctures an anatomical cavity to provide communication with the inside of the cavity.

(2) Brief Description of the Prior Art

Endoscopic surgical procedures gain access to the inside of an anatomical cavity by using an implement, such as a trocar, cannula, or a needle having a sharpened point to pierce or puncture the bodily tissues, muscles, membranes, or the like, which may form a portion or surround the cavity wall. A surgical needle, for example, connected to a catheter may be used to pierce a cavity in a blood vessel, subarachnoid space, heat ventricle, or the like. After piercing such cavity, the needle is left in situ and used to inject or withdraw gases or liquid phase fluids from the cavity or to insufflate the cavity by injection of, for example, a particular inert gas or other fluid.

Similarly, in many endoscopic procedures, a small incision may be made in the skin of a patient along the abdomen, for example, and the sharp point of a larger penetrating implement, such as a trocar of suitable length and diameter, is inserted into the incision, and pushed until the point punctures the cavity wall. Thereafter, a sleeve is slid over the exterior surface of the implement into the puncture wound to serve as a lining for preserving the shape of the passageway created by the implement. After the sleeve is in place, the implement may be withdrawn and an endoscope, or other operating instrument, may be inserted via the sleeve to view and operate upon organs within the cavity.

Penetrating the wall of an anatomical cavity with a surgical puncturing instrument can be quickly done and usually creates a small, neat, passageway providing communication to the interior of the cavity. While the sharp point of a penetrating implement is being pushed through a cavity wall, it encounters great resistance from the tissue, muscle and membranes forming the cavity wall. Once the sharp point and blade of the implement pass through the cavity wall and into the cavity, the resistance drops significantly. Due primarily to the shape of the instrument relative to the hand of the surgeon, the sharp point of the implement, however, can easily injure organ structure within the cavity upon the slightest contact.

Heretofore unless the surgeon stopped pushing the implement just as soon as penetration is complete, there has been a grave risk that the implement will continue penetrating deeply into the cavity and injure neighboring organ structures. If an unintended bodily member is injured by the point of the implement, unless an immediate and massive hemorrhage occurs, the injury may not become apparent until long after completion of the surgery. At a minimum, such an injury will delay a patient's recovery and may seriously endanger the patient's health. Accordingly, it has been observed the "pushing" or application of "thrust" while manipulating the instrument during surgery is not desirable.

Often, a preliminary, precautionary procedure is taken, particularly prior to penetration of the pelvic or abdominal cavities, in an effort to reduce the risk of injuring interior anatomical structures. After a small incision is made, a Verres-like needle or a small diameter safety endoscope, or the like, is first used to puncture the cavity wall. Thereafter, a gas, such as carbon dioxide, is next introduced into the cavity to create pneumoperitoneum, or insufflation, causing the cavity wall to bulge outwardly and separate from the organ structure inside the cavity. Then, a larger implement such as a trocar, may be used to puncture the cavity wall with a lower risk of injuring other organ structures subsequent to penetration. Despite this precautionary procedure, there are still significant incidents of injury to bowels, blood vessels, and omenta due to inadvertent contact with the sharp troccar or other needle-like configuration at the end of the surgical instrument which may be moved inside the body by even minor application of thrust with the surgeon's hand.

During pneumoperitoneum, it is extremely desirable to have a fluid passageway through the insufflation instrument to maximize flow of the insufflating fluid, such as inert gas, thereby reducing the time required to complete the pneumoperitoneum or insufflation procedure in the surgical operation.

Additionally, prior art insufflation instruments have an inner cylindrical member which has its distal end closed by means of a rubber, elastomeric, plastic or other member which typically is glued or ultrasonically secured to the inner cylindrically member. Thus, the inner cylindrically member comprises two components, which are secured one to another. Because the means for securing such members, one to another, are chemical in nature, resulting in a bonding or adhesive force, the chances of separation of the tip end of the inner cylindrical member while it is inserted through the abdominal wall during surgery, is a significant negative deterrent to such design.

Typically, such insufflation instruments will have a valving structure sealingly engageable through the proximal end of the device, with a valve element therein being manually manipulatable between opened and closed positions to control the flow of a fluid such as the insufflating gas, through a passageway through one of the cylindrical members, such as carbon dioxide through the inner of the cylindrical members. A cap element is required to be inserted onto the housing of the apparatus for receipt of such a valve element. Again, gluing or ultrasonically bonding of such elements reduces the sealing and securing integrity between the housing and such cap.

When and if the needle-like configuration of the distal end of the outer-most member of the cylindrical members forming the device, typically, passes through the abdominal wall, the inner member, defining the fluid transmission passageway therein, will be permitted to expansively telescope. Such expanded telescopic position can be visually viewed through an indicator, typically located in the housing at the proximal end of the apparatus. As surgery continues, if the distal end of the apparatus contacts an organ, blood vessel, or the like, and too much thrust force is applied through the apparatus toward such organ, the inner of the cylindrical members will overcome the bias force and will contract, thus dangerously exposing the needle-like configuration on the distal end of the outer-most cylindrical member. To indicate the occurrence of such an event, such an insufflation apparatus will have a visual indicator in the housing to indicate the positioning of the members resulting from such an occurrence. However, in the past, quick, positive and confirmed location, visually, of such indicator, has been somewhat difficult, due to poor visibility through the housing structure.

In an insufflating instrument, it is most desirable for the surgeon to have as much "feel" for the positioning and location of the instrument inside an incision or while making an incision into the abdominal wall. As stated above, use of "thrust" is not preferable, thus, any such device, the design of which encourages the use of thrust is of inferior design.

The present invention addresses the problems and deficiencies of the prior art, as discussed above.

SUMMARY OF THE INVENTION

In one embodiment, the present invention provides a surgical insufflation instrument which comprises first and second elongate cylindrical members. The cylindrical members are concentrically disposed relative to one another with the first of the members being telescopically movable between retracted and expanded positions relative to the second cylindrical member. One of the cylindrical members defines at its distal end a needle-like configuration, and the other of the cylindrical members has an outer surface continuously extending to define a diametrically closing end thereof, said closing end having a fluid-transmitting opening therethrough. A fluid transmitting passageway is defined within the other of the cylindrical members and extends from one end thereof to the other end thereof and communicates with the fluid-transmitting opening. The other of the cylindrical members has at least one secondary fluid-transmitting protrusion therethrough and in communication with the fluid-transmitting passageway.

In another embodiment, the surgical insufflation instrument has first and second elongate cylindrical members concentrically disposed relative to one another and telescopically movable between retracted and expanded positions. One of the cylindrical members defines at the distal end thereof a needle-like configuration, and the other of said members has a fluid-transmitting protrusion therethrough. A fluid-transmitting passageway within the other of the cylindrical members extends from one end thereof to the other end, and communicates with the fluid-transmitting protrusion. Biasing means are provided for biasing the other cylindrical member toward the expanded position. Means are provided immediate the proximal end of the cylindrical member for visually indicating at least one telescopically expanded and contracted positions of said cylindrical members. Housing means are provided for receipt of the proximal ends of each of the cylindrical members and for grasping the apparatus by hand in a dart-like mode to avoid holding the device in a manner which encourages application of thrust.

The device also may have means including a housing surrounding the proximal ends of the cylindrical members and having a series of radially spaced opacified facets for enhancing visual observation of the position of the cylindrical members relative to one another. In one embodiment, the cylindrical member indicator section has a series of radially spaced opacified elements having contourly sloping surfaces extending from an exterior apex line.

In still another embodiment, the surgical insufflation instrument consists of first and second elongate cylindrical members concentrically disposed relative to one another and telescopically movable between retracted and expanded positions. A housing is provided which surrounds the proximal end of the cylindrical members, with the housing receiving a cap member at its outboard-most end. Securing means are provided between the housing and the cap and include a tapered receptacle portion on either the housing or the cap having an interiorally receding line of taper. A tapered entry portion is provided on the other of the housing and the cap which is contourly tapered relative to the taper on the housing. A radially extending snap portion is provided on the taper of the cap or the housing, and a receptacle is defined on the taper of the other of the cap and the housing for engaging interception of said portion, to thereby join the housing and the cap.

The present invention thus provides an insufflation instrument which eliminates dual components forming the interior concentric tubular member through which a fluid, such as gas, passes during insufflation, by providing an inner tubular member which has its walls extended, such as by extrusion or rolling to a closed end through which a small opening for transmission of fluid therethrough, such as gas, is made. By designing the apparatus in such fashion, the possibility of separation of the tip end of the inner cylindrical member from the cylindrical member while the device is within the abdomen during surgery is eliminated. By providing a fluid passageway through such tip, fluid flow during insufflation is enhanced when it is combined with fluid flow through the other fluid flow portal offset from the end but proximal thereto.

The present invention also elements the tendency to insert the device through the abdominal wall by eliminating the necessity of thrust resulting from or providing a housing configuration for the cylindrical members which permits the apparatus to be held by the surgeon in a dart-like mode. Accordingly, the configuration of the housing of the present invention permits the surgeon to feel the piercing of the needle through skin when the skin is grasped and pinched for insertion of the apparatus in a very delicate manner.

DESCRIPTION OF THE PREFERRED EMBODIMENTS

Figure 1:
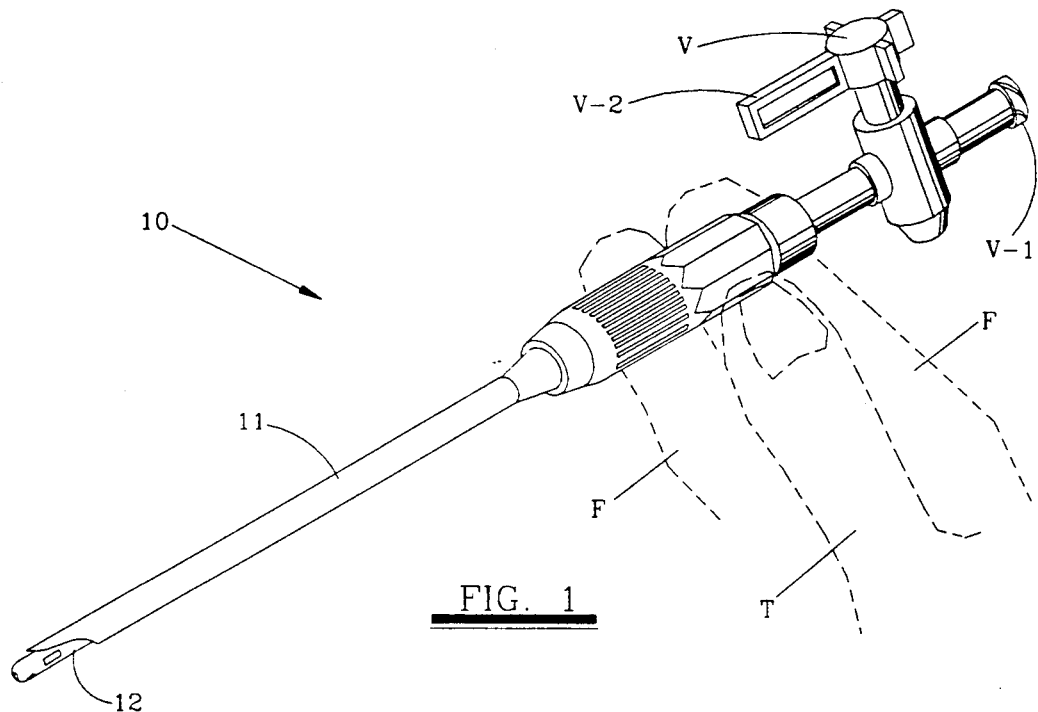
FIG. 1 is a perspective illustration of the insufflation instrument of the present invention being held in dart-like mode in the fingers of a surgeon, with the concentric members being in telescopically expanded and biased position.

Now, with first reference to FIG. 1, there is shown an insufflation instrument 10 having a first elongate cylindrical member and a second elongate cylindrical member 12 concentrically disposed interiorally therein. As shown, the instrument 10 is held in dart-like position by means of light application of the tips of a surgeon's fingers F and thumb T. At the proximal end of the insufflation instrument 10 is shown a conventional valve assembly V with a hand-manipulatable valve actuator V-2 thereon for manipulating between open and closed positions a ball or other valve mechanism (not shown). The valve assembly V has an opening V-1 therein for receipt of a fluid transmission line, (not shown) such as for gas, or the like.

Figure 2A:
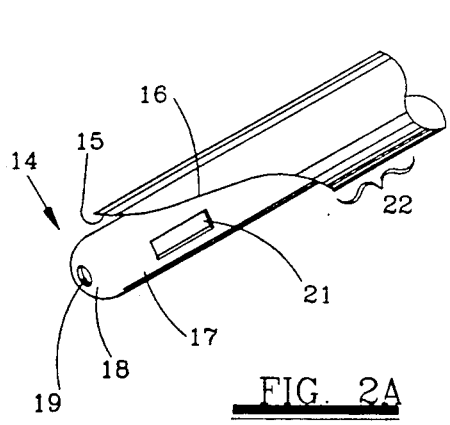
FIG. 2A is an enlarged perspective illustration of the distal end portion of the concentric members illustrating the tip distal end of the innermost cylindrical member and the fluid passages through such member, with the cylindrical members in expanded position.
Figure 2B:
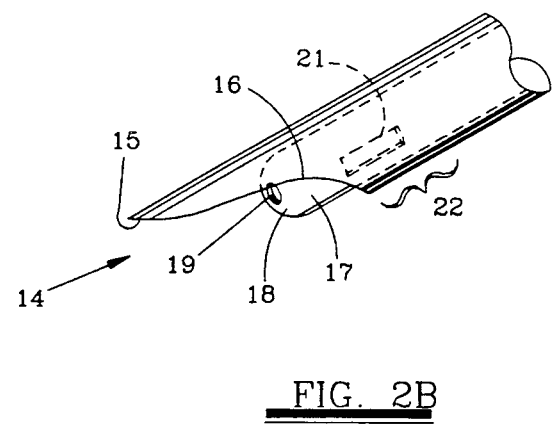
FIG. 2B is a view similar to FIG. 2A, but showing the secondary fluid transmission opening being shielded when the cylindrical members are in contracted position.

Now referring to FIGS. 2A and 2B, the first elongate cylindrical member 11 has at its distal end 15 a needle-like configuration 16 and a shielding portion 22. As shown in FIG. 2A, the insufflation instrument 10 is shown in the expanded position 14.

The second elongate cylindrical member 12 has an outer surface 17 which is extended, such as by extrusion or rolling, into a diametric closing end 18, thus making the second elongate cylindrical member 12 a complete one-piece element. A small central first transmitting opening 19 is defined through the diametrically closing end 18, and preferably may have a diameter of about .0060 inch. As shown in FIG. 2A, the opening 19 has an angle of approximately 90 degrees relative to the outer surface 17.

The purpose of providing the first transmitting protrusion 19 through the diametrically closing end 18 is to enhance the rate of fluid flow through the interior of the second elongate cylindrical member 12 from the fluid transmission line (not shown) received through the opening V-1 of the valve assembly V and through the interior of the second elongate cylindrical member 12 of the instrument 10, during insufflation. The elongate cylindrical member 12 also is provided with a secondary fluid transmission opening 21, shown in FIG. 2A as rectangular in shape.

Figure 3:
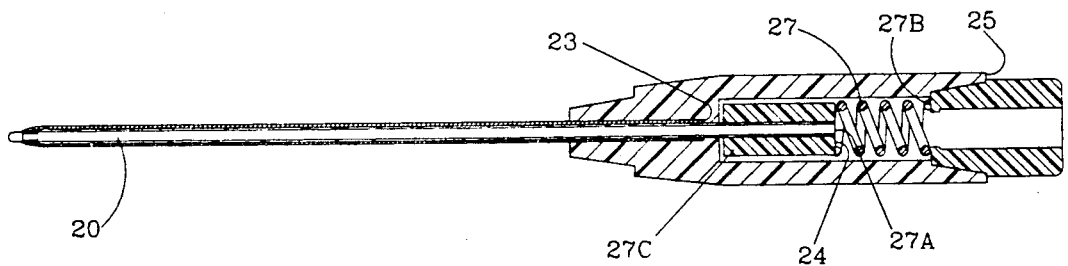
FIG. 3 is a longitudinal sectional view of the apparatus of the present invention, in the position shown in FIG. 1.
Figure 4:
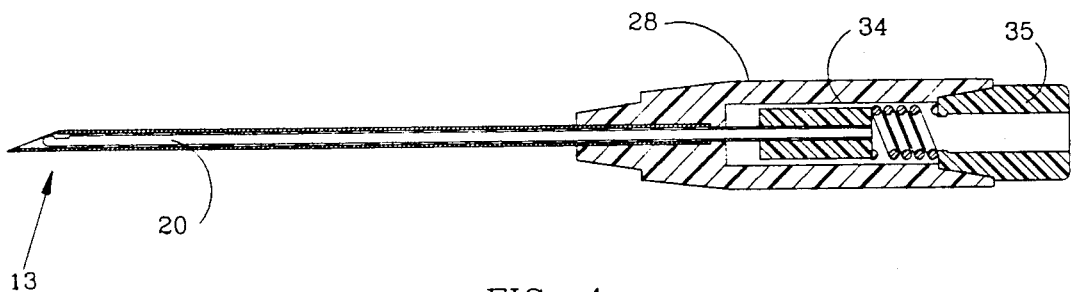
FIG. 4 is a view similar to FIG. 3, showing the concentric members in telescopically retracted position.

Now referring to FIGS. 3 and 4, the first fluid transmitting opening 19 and the secondary fluid transmission opening 21 each communicate with a central fluid transmission passageway 20 defined within the interior of the second elongate cylindrical member 12. The fluid transmission passageway 20 extends through the interior of the housing 28 of the instrument 10, through the cap 35 secured thereto, and through the valve assembly V.

Each of the elongate cylindrical members 11, 12, have their respective proximal ends 23, 24 secured within the interior of the housing 28.

The second elongate cylindrical member 12 is biased to the telescopically expanded position relative to the first elongate cylindrical member 11 by biasing means which include a spring member 27 housed within the housing 28 having an end 27A abutting an end of an enlarged spring arrestor 27C carried by the second elongate cylindrical member 12. The other end 27B of the spring 27 abuts the interior face of a cap member 35.

The housing 28 has a proximal end 25 facing the cap 35 and the valve assembly V.

The bias in the spring 27 normally urges the second elongate cylindrical member 12 to the expanded position 14, as in FIGS. 1, 2A and 3. Upon contact with human tissue or a human organ, during surgery, sufficient to overcome the bias in the spring 27, the second elongate cylindrical member 12 will move to the telescopically contracted position relative to the first elongate cylindrical member 11, compressing the spring 27 (FIG. 4) and moving the insufflation instrument 10 to the retracted position 13 (FIG. 4).

Figure 5:
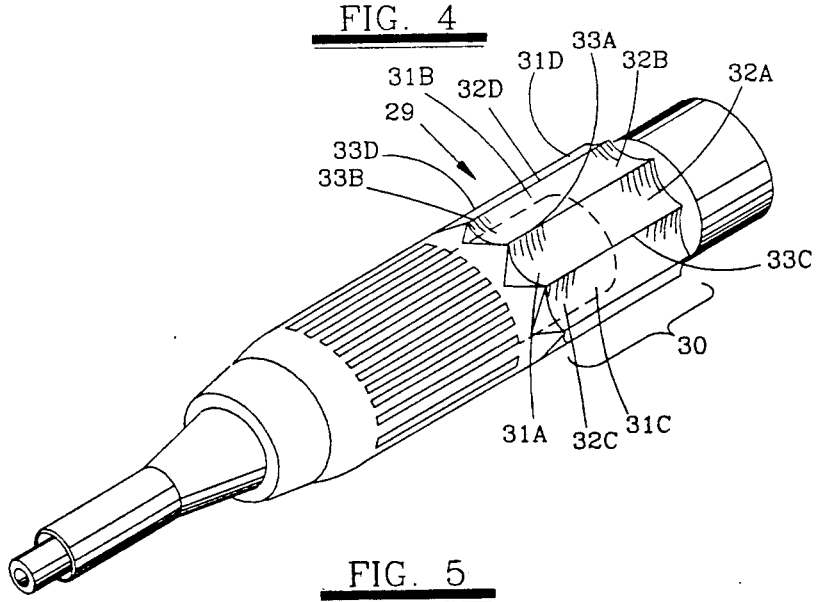
FIG. 5 is a perspective view of the proximal end of the apparatus, illustrating the means for visually enhancing the telescopic position of the cylindrical members.
Figure 6:
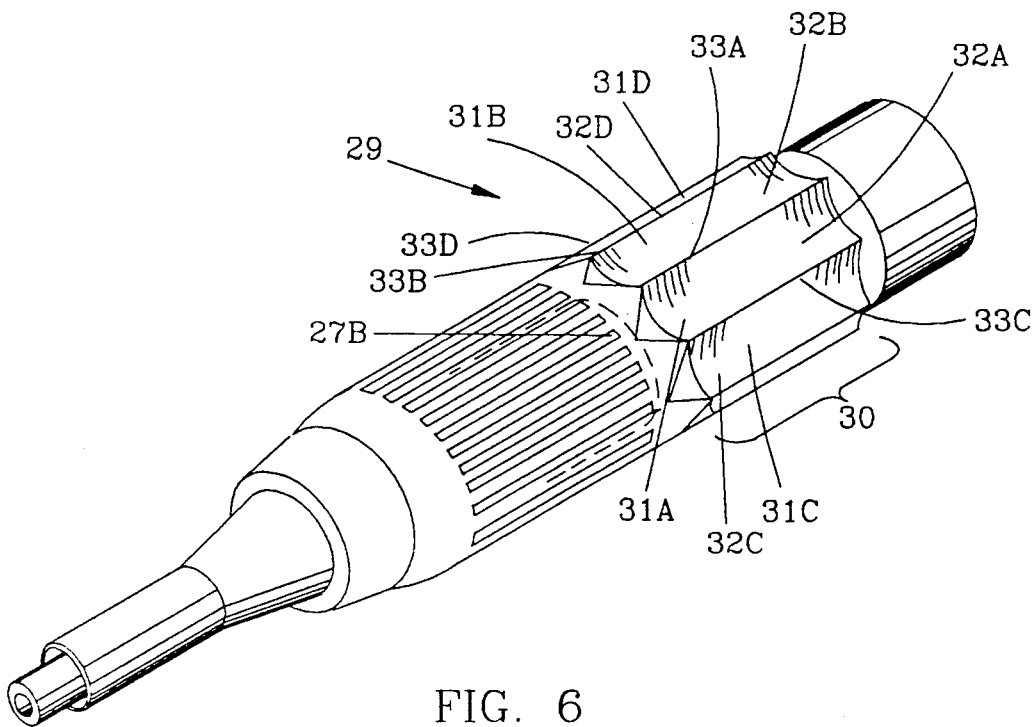
FIG. 6 is a view similar to that of FIG. 5, illustrating the viewing through the visual enhancement portion of the housing when the concentric members are in relative expanded position.

Now referring to FIG. 5, it should be noted that the spring arrestor 27C serves the dual function of directing the bias in the spring 27 to the second elongate cylindrical member 12. Of equal importance, the position of the spring arrestor 27C within the housing 28 serves as an indicator, by visual observation, of the relative position between the elongate cylindrical members 11 and 12. As shown in FIG. 5, the spring arrestor 27C is in position indicating that the second elongate cylindrical member 12 is in contracted position relative to the first member 11, upon sufficient contact with human tissue or an organ, during surgery, while FIG. 6 shows the normal telescopic expanded mode of the cylindrical members 11, 12, and the spring arrestor 27B being positioned in housing 28 to so indicate.

The housing 28 provides a transparent indicator section 30 which consists of a series of radially defined facets 31A, 31B, 31C and 31D, completely around the exterior of the housing 28. Each of the facets 31A, 31B, 31C, 31D is defined by a sloping surface 32A, 32B, 32C and 32D, with each sloping surface peaking at respective apex lines 33A, 33B, 33C and 33D. The interior of the transparent indicator section 30 has a flat surface 34. (FIG. 4). The housing 28, preferably being made of an opaque plastic or other similar material thus will have a transparent indicator section 30 having the facets, as indicated, and a flat inner surface 34. Accordingly, vision through the housing 28 is thus somewhat enlarged, to further enhance viewing of the position of the spring arrestor 27C.

To further enhance the vision of the position of the spring arrestor 27C within the housing 28 and through the transparent indicators section 30, the spring arrestor 27C may be colored a bright contrasting color, such as blue, red, green, or the like.

Figure 7:
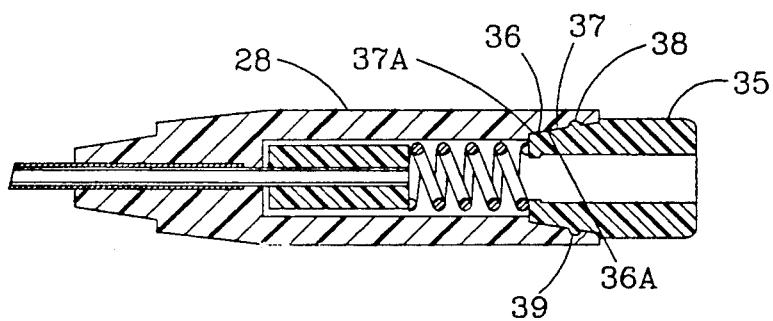
FIG. 7 is a longitudinal sectional view of the housing for the concentric members illustrating the snap securement of the cap relative to the housing.
Figure 8:
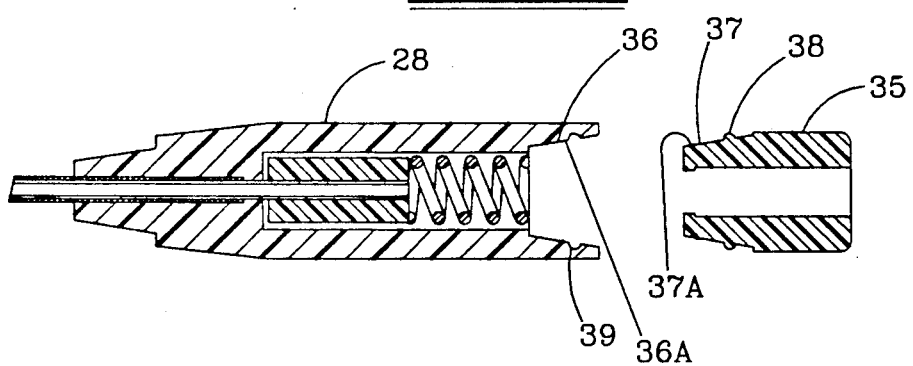
FIG. 8 is a view similar to that of FIG. 7 particularizing the relative tapers of the cap and the housing prior to insertion of the cap into the housing.

Now referring to FIGS. 7 and 8, the housing 28 has a cap 35 secured thereto which receives the valve assembly V. The housing 28 has a tapered receptacle 36 within an internally receding line of taper 36A for receipt of a companion receding taper line 37A on a tapered entry portion 37 of the cap 35. An outwardly protruding latch or circularly extending snap 38 is defined in the tapered entry portion 37 of the cap 35, while the tapered receptacle 36 has a groove or snap receptacle 39 defined on the internally receding line of taper 36A.

Accordingly, when it is desired to secure the cap 35 to the housing 28, the parts will move into engagement with one another as the respective taper lines 37A, 36A, move into contact. The snap 38 will cause the cap 35 to flex inwardly, just slightly, as it is moved into position in the housing 28. When the snap 38 comes into alignment with the receptacle 39, the snap 38 will flex, just slightly, outwardly and the snap receptacle 39 will resist further internal movement of the cap 35 relative to the housing 28. Additionally, the cap 35 will be sealed into the housing 28 by means of the complementary line between the tapers 36A, 37A. An O-ring seal (not shown), or other secondary seal, may be provided between the surfaces of the tapers 36A, 37A, on one of the members 28, 35 to further seal the members relative to one another.

Accordingly, the cap 35 will be secured in the housing 28, as shown in FIG. 7. This means of securing the cap 35 relative to the housing 28 avoids the use of glue, or other chemical means, and further ensures the integrity of the sealing and securing relationship between the cap 35 and housing 28.

Although the invention has been described in terms of specified embodiments which are set forth in detail, it should be understood that this is by illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed and desired to be secured by Letters Patent is:

1. A surgical insufflation instrument, comprising: first and second elongate cylindrical members, said members being concentrically disposed relative to another, the first of said members being telescopically movable between retracted and expanded positions relative to the second of the cylindrical members, one of said cylindrical members defining at its distal end a needle-like configuration, and the other of said cylindrical members having its outer surface continuously extending to define an oval shaped closing end thereof, said closing end having a first fluid-transmitting opening therethrough; and a fluid-transmitting passageway within said other of said cylindrical members extending from one end thereof to the other end thereof and communicating with said first fluid-transmitting opening.

2. The insufflation instrument of claim 1, said other of said cylindrical members having at least one secondary fluid-transmitting opening therethrough and in communication with said fluid-transmitting passageway.

3. The insufflation instrument of claim 2, said first and second cylindrical members being aligned whereby when said first and second members are moved to the relative telescopic expanded position, each of said secondary fluid-transmitting openings is positioned away from said needle-like configuration to enhance fluid transmission flow therefrom.

4. The insufflation instrument of claim 3; and a shielding portion on said one of said cylindrical members whereby, when said first and second members are moved to the relative telescopically contracted position, each of said secondary fluid-transmitting openings is interiorly shielded by said shielding portion.

5. The insufflation instrument of claim 1 wherein the outer surface of said other of said cylindrical members circularly extends relative to the outer diameter of the other of said cylindrical members at an angle of about 90 degrees, to said fluid transmitting opening.

6. The insufflation instrument of claim 1 further including means for biasing the other of said cylindrical members toward the expanded position.

7. A surgical insufflation instrument, comprising: inner and outer elongate cylindrical members, said members being concentrically disposed relative to one another, the inner of said members being telescopically movable between retracted and expanded positions relative to the outer of the cylindrical members, said outer cylindrical member defining at its distal end a needle-like configuration, and the inner of said cylindrical members having its outer surface continuously extending to define an oval shaped closing end thereof, said closing end having a first fluid-transmitting opening therethrough; and a fluid-transmitting passageway within said inner cylindrical member extending from one end thereof to the other end thereof and communicating with said first fluid-transmitting opening.

8. The insufflation instrument of claim 7 wherein said inner cylindrical member includes at least one secondary fluid-transmitting opening therethrough and in communication with said fluid transmitting passageway.

9. The insufflation instrument of claim 8 wherein said cylindrical members are aligned whereby when said members are moved to the relative telescopic expanded position, each of the secondary fluid-transmitting openings is positioned away from the needle-like configuration to enhance fluid transmission flow therefrom.

10. The insufflation instrument of claim 9 further including: a shield portion on the outer of said cylindrical members whereby, when said members are moved to the relative telescopic contracted position, each of the secondary fluid-transmitting openings is interiorly shielded by said shield portion.

11. The insufflation instrument of claim 7 wherein the outer surface of the outer of said cylindrical members circularly extends relative to the outer diameter of the outer cylindrical member at an angle of about 90 degrees, to said opening.

12. The insufflation instrument of claim 7 further including means for biasing the inner of said cylindrical members toward the expanded position.

13. A surgical insufflation instrument, comprising: first and second elongate cylindrical members, said members being concentrically disposed relative to one another, the first of said members being telescopically movable between retracted and expanded positions relative to the second of the cylindrical members, one of said cylindrical members defining at the distal end a needle-like configuration, and the other of said members having a fluid-transmitting opening therethrough; a fluid-transmitting passageway within said other of said cylindrical members extending from one end thereof to the other end thereof and communicating with said fluid-transmitting opening; biasing means for biasing said other cylindrical member toward the expanded position; means immediate the proximal end of said cylindrical members for visually indicating at least one of telescopically expanded and contracted positions of said cylindrical members; and housing means receiving the proximal ends of each of said cylindrical members and for grasping said apparatus by hand in a dart-like mode, said housing means including a transparent cylindrical member indicator section, said indicator section receiving the proximal end of said other cylindrical member when said cylindrical members are in the relative contracted position.

14. The insufflation instrument of claim 13, said housing means including a series of radially spaced opacified facets for enhancing visual detection of the expanded and contracted positions of said cylindrical members.

15. The insufflation instrument of claim 13, said cylindrical member indicator section having at least one opacified facet portion thereon for visually enhanced detection of the relative contracted position of said cylindrical members.

16. The insufflation instrument of claim 13 further including at least one radially spaced opacified facet having contourly sloping surfaces extending from an exterior apex line for enhancing visual detection of the expanded and contracted position of said cylindrical members.

17. A surgical insufflation instrument, comprising: first and second elongate members, said members being concentrically disposed relative to one another, the first of said members being telescopically movable between retracted and expanded positions relative to the second of the cylindrical members, one of said cylindrical members defining at the distal end a needle-like configuration, and the other of said members having a fluid-transmitting opening therethrough; a fluid-transmitting passageway within said other of said cylindrical members extending from one end thereof to the other end thereof and communicating with said fluid-transmitting opening; biasing means for biasing said other of said cylindrical members toward the expanded position; a housing surrounding the proximal ends of said cylindrical members, said housing receiving a cap member at its outboard-most end; securing means between said housing and said cap member including a tapered receptacle portion on one of said housing and such cap member having an internally receding line of taper; a tapered entry portion on the other of said housing and said cap member contourly tapered relative to the taper on said housing, a radially extending snap portion on the taper of one of said cap member and said housing, and a snap receptacle on the taper of the other of said housing and said cap member for engaging interception of said snap portion to thereby join said housing and said cap member.

* * * * *